United States Patent
Shintou et al.

(10) Patent No.: US 6,437,203 B1
(45) Date of Patent: Aug. 20, 2002

(54) PROCESS FOR PRODUCING IODINATED AROMATIC COMPOUNDS

(75) Inventors: Taichi Shintou; Satoru Fujii; Shinji Kubo, all of Kanagawa (JP)

(73) Assignee: Sankio Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/567,434

(22) Filed: May 10, 2000

(30) Foreign Application Priority Data

May 10, 1999 (JP) .......................................... 11-128739

(51) Int. Cl.$^7$ ........................ C07C 17/00; C07C 209/00
(52) U.S. Cl. ....................................... 570/206; 564/412
(58) Field of Search ........................... 570/206; 564/412

(56) References Cited

U.S. PATENT DOCUMENTS

| 4,567,280 A | | 1/1986 | Itatani et al. |
| 4,898,999 A | * | 2/1990 | Corley ........................ 570/207 |
| 5,856,596 A | | 1/1999 | Nukada |

FOREIGN PATENT DOCUMENTS

JP 63-91336 4/1988

* cited by examiner

*Primary Examiner*—Alan Siegel
(74) *Attorney, Agent, or Firm*—Sughrue Mion, PLLC

(57) ABSTRACT

Disclosed is a process for producing an iodinated aromatic compound, which comprises reacting an aromatic compound with an iodine compound in the presence of a chlorate as an oxidizing agent.

20 Claims, 1 Drawing Sheet

PROCESS FOR PRODUCING IODINATED AROMATIC COMPOUNDS

FIELD OF THE INVENTION

The present invention relates to a process for producing an iodinated aromatic compound at a low cost and a high purity.

BACKGROUND OF THE INVENTION

Iodinated aromatic compounds are used as an important intermediate in the production of organic photoreceptors to be used for electrophotography, organic electroluminescent device or the like, dyestuffs, agricultural chemicals, pharmaceuticals and the like.

Iodinated aromatic compounds can generally be synthesized by the Sandmeyer reaction of corresponding aromatic amino compounds (*Bull. Soc. Chem.*, 7, 634(1940)) or by directly iodinating aromatic compounds.

The process using the Sandmeyer reaction is not industrially preferred, because aromatic amino compounds employed for the reaction tend to have strong toxicity and moreover, post-treatment after reaction is complicated and a production yield is low.

In the latter process for directly iodinating an aromatic compound, on the other hand, an oxidizing agent and if necessary, a reaction solvent and an acid catalyst are used upon reacting the aromatic compound with an iodine compound. Concerning the use of an oxidizing agent, conventionally known are a process using peracetic acid (*J. Am. Chem. Soc.*, 90, 6187(1968), *J. Chem. Soc. Perkin I*, 180 (1972)), a process using iodic acid (Ann., 634, 84(1960)), a process using periodic acid (*Journal of the Chemical Society of Japan*, 92(11), 1021(1971)), and a process using a silver salt such as silver nitrate or silver sulfate, or silver trifluoroacetate (*J. Am. Chem. Soc.*, 73, 1362(1951), *Tetrahedron Lett.*, 30 (29), 3769(1989), *Synth. Commun.*, 20(6), 877 (1990)). The use of such an oxidizing agent increases a cost, because it is expensive and the disposal of its waste liquid is required.

A process using nitrogen dioxide (U.S. Pat. No. 4,567, 280) and a process using nitric acid (*J. Org. Chem.*, 42(25), 4049(1977)) as an oxidizing agent are also known. These processes are however accompanied with the problems in that an aromatic nitro compound is byproduced when such an oxidizing agent is used, which makes the purification difficult, and an oxidized nitrogen gas is generated from the reaction system or some aromatic nitro compounds byproduced have strong toxicity, leading to difficulty in taking countermeasures against environmental pollution.

Further, a process (JP-A-63-91336) using hydrogen peroxide and a process (JP-A-49-14527) using a persulfate are known. These oxidizing agents however need care upon handling and do not bring about a high yield.

When a large excess of an aromatic compound is used relative to an iodine compound as in mono-iodination (U.S. Pat. No. 5,856,596), the aromatic compound which has remained after reaction must be separated by post-treatment. When the aromatic compound has a high boiling point, separating operation such as solid distillation using special equipment becomes a cause for a high cost.

SUMMARY OF THE INVENTION

An object of the present invention is to provide a process for producing a high-purity iodinated aromatic compound at a low cost, while neither using a highly toxic raw material nor substantially forming a byproduct.

In the present invention, there is thus provided the below-described process for producing an iodinated aromatic compound and the object of the present invention is attained by the process.

That is, the present invention provides a process for producing an iodinated aromatic compound, which comprises reacting an aromatic compound with an iodine compound in the presence of a chlorate as an oxidizing agent.

DETAILED DESCRIPTION OF THE INVENTION

Figure 1:
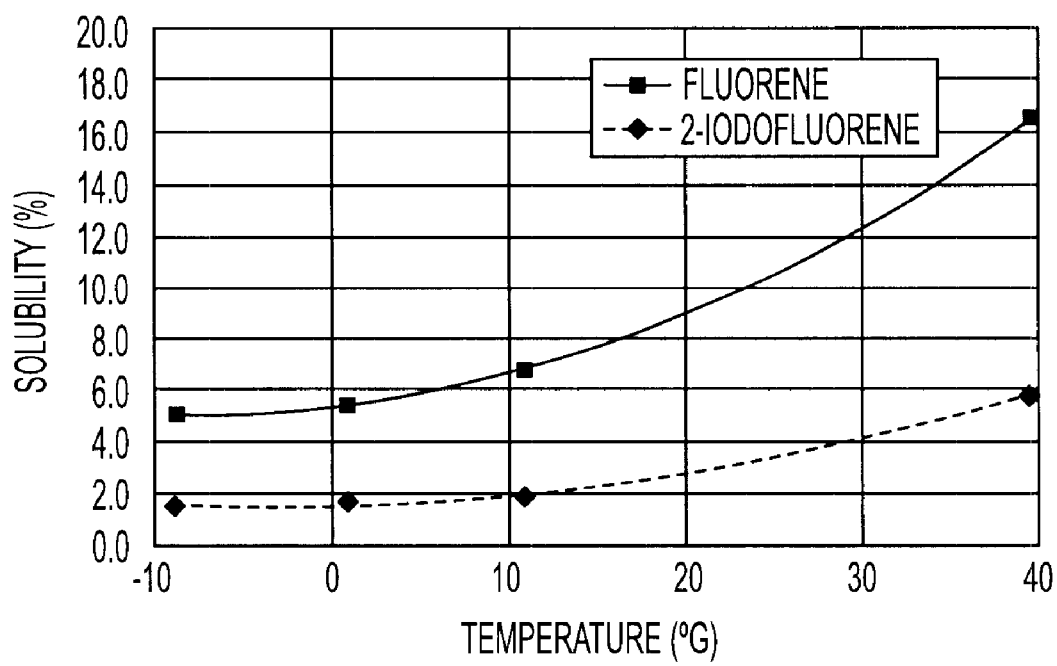
FIG. 1 is a graph illustrating temperature dependence of the solubilities of fluorene and 2-iodofluorene in the crystallization solvent system of Example 1.

The present invention will hereinafter be described more specifically.

Although there is no particular limitation imposed on the aromatic compound to be iodinated in the production process of the present invention, those which have conventionally been iodinated by the direct iodination method can be mentioned as examples. Specific examples include substituted benzenes such as toluene, mesitylene, aniline and anisole, condensed polycylic aromatic compounds such as naphthalene, anthracene, phenanthrene and pyrene, aromatic compounds having a plurality of non-condensed aromatic rings such as diphenyl, terphenyl, fluorene, diphenylether, diphenylamine and triphenylamine; heterocyclic aromatic compounds such as dibenzofurane, dibenzothiophene and carbazole. It is needless to say that the aromatic compound is not limited by these specific examples.

No particular limitation is imposed on the iodine compound to be used in the present invention insofar as the above-exemplified aromatic compound can be iodinated by it. Preferred examples include iodine, hydroiodic acid, potassium iodide and sodium iodide, of which iodine is more preferred because of a high reaction rate.

The using ratio of the aromatic compound to the iodine compound is suitably selected, depending on the number of iodine to be introduced into one molecule of the aromatic compound.

For the mono-iodination of the aromatic compound, the aromatic compound is used in at least an equimolar amount relative to the iodine compound in order to suppress the formation of a di-iodine derivative. When the ratio of the aromatic compound is excessively large, unreacted aromatic compounds remain upon the purification step, for example, separation and purification by the crystallization method. The aromatic compound is therefore preferably used in an amount ranging from 1.5 to 4.0 molar times, more preferably from 2.0 to 3.0 molar times, relative to the iodine compound.

For the di-iodination of the aromatic compound, the aromatic compound is preferably used in an amount ranging from 0.3 to 0.7 molar time, more preferably from 0.5 to 0.6 molar time, relative to the iodine compound.

For the tri-iodination of the aromatic compound, the aromatic compound is preferably used in an amount ranging from 0.1 to 0.5 molar time, more preferably from 0.3 to 0.4 molar time, relative to the iodine compound.

Although there is no particular limitation imposed on the chlorate to be used as an oxidizing agent in the production process-of the present invention, commercially available sodium chlorate and potassium chlorate are preferably used, of which sodium chlorate is cost-wisely preferred. Chlorates can be used either singly or in combination.

The use of a chlorate as an oxidizing agent makes it possible to complete the reaction in a considerably short time. It usually takes only 0.5 to 1 hour to complete the reaction.

The use of a hypochlorite, chlorite, perchlorate, bromate, iodate or the like, on the other hand, remarkably prolongs the reaction time and is therefore industrially undesired.

The chlorate is used in an amount ranging from 0.15 to 1 mole, more preferably from 0.17 to 0.4 mole, still more preferably from 0.18 to 0.33 mole, per mole of the iodine atom of the above-described iodine compound. Amounts of the chlorate smaller than the above-described range prolong the reaction time, while larger amounts deteriorate the yield.

The chlorate as an oxidizing agent is presumed to oxidize hydrogen iodide or an iodine salt which exists in the reaction system or is formed by the reaction, thereby iodinating the aromatic compound efficiently.

Although the production process of the present invention does not need a catalyst, the use of an acid catalyst as needed is preferred because it terminates the reaction in a shorter time. Examples of the acid catalyst include inorganic acids such as sulfuric acid, hydrochloric acid and a mixture of sulfuric acid and nitric acid; organic acids such as p-toluenesulfonic acid; peroxides such as peracetic acid and persulfates; and solid acid catalysts such as strongly acidic ion exchange resin. Among them, sulfuric acid and p-toluenesulfonic acid are preferred, of which sulfuric acid is more preferred because it is inexpensive and terminates the reaction in a short time. These acid catalysts can be used either singly or in combination.

The acid catalyst is preferably used in an amount of at least 2.0 equivalents, more preferably in an amount ranging from 2.3 to 2.7 equivalents relative to the amount of a chlorate used. Amounts less than 2.0 equivalents relative to the chlorate do not bring about marked reaction accelerating effects. When the amount is too large, on the other hand, it takes much cost to dispose of the acid waste liquid. Amounts outside the above-described range are therefore not preferred from the viewpoint of industrial production.

Iodination is effected by adding predetermined amounts of an aromatic compound, an iodine compound and a chlorate as an oxidizing agent, and if necessary, an acid catalyst and a reaction solvent and then stirring the resulting mixture under heat.

During the iodination, iodine sublimes and sticks to a reactor so that with a view to preventing precipitation of iodine, it is preferred to carry out iodination while to heating the mixture under reflux in a reaction solvent.

Examples of the reaction solvent include halogenated hydrocarbon solvents such as dichloromethane, dichloroethane, trichloroethane, chloroform, chlorobenzene and o-dichlorobenzene; aromatic nitro compounds such as nitrobenzene and nitrotoluene; and carboxylic acids such as acetic acid and trifluoroacetic acid. Preferred examples of the reaction solvent include halogenated hydrocarbons having a boiling point of 120° C. or lower, acetic acid, a mixed solvent of acetic acid and water, and mixed solvents of these three components.

The solvent is preferably used in an amount ranging from 10 to 2000 ml, more preferably from 50 to 1200 ml per mole of the aromatic compound. When the using amount is too small, the crystals formed from sublimed iodine remain in the reactor and tend to cause a deterioration in the yield, while too large amounts lower the productivity, leading to a cost increase.

The reaction is preferably effected at a temperature of 160° C. or lower, more preferably from 30 to 150° C., most preferably from 40 to 120° C.

The reaction mixture is then subjected to post-treatment composed of the below-described steps (I) to (III), whereby the crude product is obtained in a high yield. A suitable method is adopted for the post-treatment, depending on the nature of the iodinated aromatic compound and it is not limited to the method composed of the following steps.

(I) A step of extracting the reaction mixture with an organic solvent such as toluene, ethyl acetate, dichloromethane, dichloroethane or chloroform.

(II) A step of washing away iodine, which remains in a trace amount in the iodinated-aromatic-compound containing solution obtained in the step (I), with an aqueous solution of sodium thiosulfate and then washing further with water.

(III) A step of purification by any one of the following (i) to (iii):
  (i) distillation of the solution, which has been washed in the step (II), under reduced pressure.
  (ii) crystallization in the solution which has been washed in the step (II).
  (iii) crystallization by adding an organic solvent such as alcohol, acetonitrile or hexane to the solution, which has been washed in the step (II).

For example, as in the case of mono-iodination, when a large amount of the unreacted aromatic compound remains in the reaction system and the unreacted aromatic compound must be separated from the iodinated aromatic compound in the post-treatment, the target compound can be isolated by the above-described step (III)-(i) if the iodinated aromatic compound thus produced has a low boiling point.

If the iodinated aromatic compound thus produced has a high boiling point, on the other hand, the step (III)-(ii) or (III)-(iii) is adopted and the target compound can be crystallized by optimizing the crystallization temperature and crystallization time. This makes it possible to produce high-quality crude crystals in a high yield without conducting solid distillation by special equipment which is a cause for cost increase.

The resulting crude crystals have a quality sufficient for use as an intermediate for an electronic material. Thus, an iodinated aromatic compound can be obtained at a low cost.

EXAMPLES

The present invention will hereinafter be described in further detail by Examples. It should however be borne in mind that the present invention is not limited by them. The purity was evaluated by high-performance liquid chromatography (which will hereinafter be abbreviated as "HPLC").

Example 1

Synthesis of 2-iodofluorene

In a 300-ml four-necked flask were charged 90 ml of glacial acetic acid and 90 ml of water, followed by the addition of 41.6 g (0.25 mole) of fluorene, 12.7 g (0.10 mole) of iodine, 1.93 g (0.018 mole) of sodium chlorate and 4.5 ml of concentrated sulfuric acid under vigorous stirring. The resulting mixture was refluxed under heat at 85 to 90° C. for 30 minutes and then at 95 to 100° C. for 30 minutes. After completion of the reaction, the reaction mixture was extracted with 55 ml of toluene. The organic layer was then washed with a 5% aqueous solution of sodium thiosulfate. After the organic layer was washed further with 50 ml of a 20% saline solution, 216 ml of methanol was added. The resulting mixture was crystallized for 2 hours at an internal temperature of 25 to 30° C. and the resulting crystals were collected by filtration. The crude crystals thus obtained were washed with 76 ml of methanol and then dried, whereby 24.8 g (yield: 84.8%) of the target compound was obtained as white crystals. As a result of HPLC analysis (column: YMC-A-312, detection UV: 254 nm, flow rate: 1.0 ml/min, eluent: methanol/water=9/1 (by volume), buffer: triethylamine and acetic acid, each 0.1%), the compound was found to be composed of 1.3% of fluorene, 98.4% of 2-iodofluorene and 0.02% of 2, 7-diiodofluorene.

FIG. 1 is a graph illustrating temperature dependence of solubility of each of fluorene and 2-iodofluorene in a mixed solvent (50 ml of toluene and 216 ml of methanol) upon the above-described crystallization. From the graph, it can be understood that at the crystallization temperature of 25 to 30° C., it is possible to efficiently separate unreacted fluorene from 2-iodofluorene while controlling the yield loss to the minimum level.

Example 2

Synthesis of 1-iodonaphthalene

In a 200-ml four-necked flask were charged 72 ml of glacial acetic acid and 72 ml of water, followed by the addition of 25.6 g (0.2 mole) of naphthalene, 8.9 g (0.07 mole) of iodine, 1.54 g (0.014 mole) of sodium chlorate and 3.6 ml of concentrated sulfuric acid under vigorous stirring. The resulting mixture was refluxed under heat at 85 to 90° C. for 30 minutes and then at 95 to 100° C. for 30 minutes. After completion of the reaction, the reaction mixture was extracted with 44 ml of toluene. The organic layer was then washed with 40 ml of a 5% aqueous solution of sodium thiosulfate. The organic layer was washed further with 40 ml of a 5% saline solution and distilled under reduced pressure to collect a fraction at an internal temperature of 78 to 80° C. and 0.5 Torr, whereby 17.3 g (yield: 85.3%) of the target compound was obtained as a pale yellow liquid. As a result of HPLC analysis (column: YMC-A-312, detection UV: 250 nm, flow rate: 1.0 ml/min, eluent: acetonitrile/water=8/2 (by volume)), the purity of 1-iodonaphthalene was found-to be 97.6%.

Example 3

Synthesis of tris (4-iodophenylamine)

In a 300-ml four-necked flask were charged 72 ml of 1, 1, 2-trichloroethane, followed by the addition of 8.59 g (0.035 mole) of triphenylamine, 16.6 g (0.10 mole) of potassium iodide, 2.33 g (0.019 mole) of potassium chlorate and 8.4 g (0.044 mole) of p-toluenesulfonic monohydrate under vigorous stirring. The resulting mixture was refluxed under heat at 105 to 110° C. for 30 minutes and then at 110 to 115° C. for 30 minutes. After completion of the reaction, the reaction mixture was crystallized overnight at an internal temperature of 10° C. or lower and then the resulting crystals were filtered out. The crude crystals thus obtained were washed with 40 ml of toluene and 100 ml of methanol and then dried, whereby 23.2 g (yield: 88.0%) of the target compound was obtained as pale yellow crystals. As a result of HPLC analysis (column: YMC-A-312, detection UV: 300 nm, flow rate: 1.0 ml/min, eluent: methanol/tetrahydrofuran=99/1 (by volume)), the purity of tris (4-iodophenyl)amine was found to be 99.5%.

Comparative Examples 1 to 10

In each of Comparative Examples 1 to 10, in a similar manner to Example 1 except that sodium chlorate was replaced by the oxidizing agent shown in Table 1, 2-iodofluorene was synthesized. The reaction time, yield and purity analyzed by HPLC of each of the resulting products were evaluated.

The results are shown in Table 1.

TABLE 1

|  | Oxidizing agent | Reaction time (hr.) | Yield (%) | Content (%) as measured by HPLC |
| --- | --- | --- | --- | --- |
| Example 1 | Sodium chlorate | 1.0 | 84.8 | 98.4 |
| Comp. Ex. 1 | Sodium hypochlorite | 20.0 < | Reaction was not completed | — |
| Comp. Ex. 2 | Sodium chlorite | 20.0 < | Reaction was not completed | — |
| Comp. Ex. 3 | Sodium perchlorate | 20.0 < | Reaction was not completed | — |
| Comp. Ex. 4 | Sodium bromate | 20.0 < | Reaction was not completed | — |
| Comp. Ex. 5 | Sodium iodate | 20.0 < | Reaction was not completed | — |
| Comp. Ex. 6 | Sodium periodate | 10.0 | 73.0 | 98.2 |
| Comp. Ex. 7 | Periodic dihydrate | 9.0 | 76.2 | 98.0 |
| Comp. Ex. 8 | Ammonium persulfate | 5.0 | 36.4 | 98.5 |
| Comp. Ex. 9 | Peracetic acid | 20.0 < | Reaction was not completed | — |
| Comp. Ex. 10 | Nitric acid | 20.0 < | Reaction was not completed | — |

As is apparent from Examples and Comparative Examples, it has been found that the use of a chlorate as an oxidizing agent makes it possible to decrease the reaction time largely and compared with the use of another oxidizing agent, the yield is excellent. In addition, chlorates, particularly, sodium chlorate is inexpensive than the ordinarily employed oxidizing agents. Judging from these advantages, the process according to the present invention is remarkably practical.

The process of the present invention makes it possible to produce, at a low cost, a highly-pure iodinated aromatic compound, which is an important intermediate in the production of organic photoreceptors to be used for electrophotography or organic electroluminescent device, dyestuffs, agricultural chemicals, pharmaceuticals or the like, while neither using a strongly toxic raw material nor substantially producing byproducts.

While the invention has been described in detail and with reference to specific embodiments thereof, it will be apparent to one skilled in the art that various changes and modifications can be made therein without departing from the spirit and scope thereof.

This application is based on Japanese patent application Hei-11-128739, filed on May 10, 1999, incorporated herein by reference.

What is claimed is:

1. A process for producing an iodinated aromatic compound, which comprises reacting an aromatic compound with iodine in the presence of a chlorate as an oxidizing agent.

2. The process for producing an iodinated aromatic compound according to claim 1, wherein the reaction is effected in the presence of an acid catalyst.

3. The process for producing an iodinated aromatic compound according to claim 2, wherein the acid catalyst is sulfuric acid.

4. The process for producing an iodinated aromatic compound according to claim 2, wherein the acid catalyst is used in an amount of at least 2.0 equivalents relative to the amount of the chlorate.

5. The process for producing an iodinated aromatic compound according to claim 2, wherein the acid catalyst is used in an amount of from 2.3 to 2.7 equivalents relative to the amount of the chlorate.

6. The process for producing an iodinated aromatic compound according to claim 1, wherein said chlorate is sodium chlorate.

7. The process for producing an iodinated aromatic compound according to claim 1, wherein said chlorate is potassium chlorate.

8. The process for producing an iodinated aromatic compound according to claim 1, wherein said chlorate is used in an amount ranging from 0.15 to 1 mole per mole of iodine.

9. The process for producing an iodinated aromatic compound according to claim 6, wherein said chlorate is used in an amount ranging from 0.15 to 1 mole per mole of iodine.

10. The process for producing an iodinated aromatic compound according to claim 7, wherein said chlorate is used in an amount ranging from 0.15 to 1 mole per mole of iodine.

11. The process for producing an iodinated aromatic compound according to claim 1, wherein said chlorate is used in an amount ranging from 0.18 to 0.33 mole per mole of iodine.

12. The process for producing an iodinated aromatic compound according to claim 6, wherein said chlorate is used in an amount ranging from 0.18 to 0.33 mole per mole of iodine.

13. The process for producing an iodinated aromatic compound according to claim 7, wherein said chlorate is used in an amount ranging from 0.18 to 0.33 mole per mole of iodine.

14. The process for producing an iodinated aromatic compound according to claim 1, wherein a reaction solvent is further added to the reaction system.

15. The process for producing an iodinated aromatic compound according to claim 14, wherein the reaction solvent is a halogenated hydrocarbon solvent.

16. The process for producing an iodinated aromatic compound according to claim 14, wherein the reaction solvent is a carboxylic acid.

17. The process for producing an iodinated aromatic compound according to claim 16, wherein the carboxylic acid is acetic acid.

18. The process for producing an iodinated aromatic compound according to claim 14, wherein the reaction solvent is a mixed solvent of acetic acid and water.

19. The process for producing an iodinated aromatic compound according to claim 1, wherein reaction is effected at a temperature of 160° C. or lower.

20. The process for producing an iodinated aromatic compound according to claim 1, wherein reaction is effected at a temperature of from 40 to 120° C.

* * * * *